United States Patent
Irby, III

(10) Patent No.: US 9,655,678 B2
(45) Date of Patent: May 23, 2017

(54) METHODS FOR THE MINIMALLY INVASIVE TREATMENT OF URINARY STONES

(71) Applicant: The Charlotte-Mecklenburg Hospital Authority, Charlotte, NC (US)

(72) Inventor: Pierce B. Irby, III, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 15/215,067

(22) Filed: Jul. 20, 2016

(65) Prior Publication Data

US 2016/0324579 A1 Nov. 10, 2016

Related U.S. Application Data

(62) Division of application No. 13/827,045, filed on Mar. 14, 2013.

(51) Int. Cl.
  *A61B 1/00* (2006.01)
  *A61B 1/04* (2006.01)
  (Continued)

(52) U.S. Cl.
  CPC .......... *A61B 18/26* (2013.01); *A61B 1/00071* (2013.01); *A61B 1/01* (2013.01); *A61B 1/018* (2013.01); *A61B 1/04* (2013.01); *A61B 1/042* (2013.01); *A61B 1/307* (2013.01); *A61B 17/22* (2013.01); *A61B 17/221* (2013.01); *A61M 25/09* (2013.01); *A61B 2017/22074* (2013.01);
  (Continued)

(58) Field of Classification Search
  CPC ..... A61B 1/00165; A61B 1/012; A61B 1/307; A61B 1/01; A61B 1/04; A61B 18/26; A61B 17/221; A61B 2017/22074
  See application file for complete search history.

(56) References Cited

U.S. PATENT DOCUMENTS

| 3,886,933 A | 6/1975 | Mori et al. |
| 4,718,406 A | 1/1988 | Bregman et al. |

(Continued)

FOREIGN PATENT DOCUMENTS

| DE | 4335783 | 4/1995 |
| DE | 102011008533 | 7/2010 |

(Continued)

OTHER PUBLICATIONS

Al-Qahtani et al., The New Olympus Digital Flexible Ureteroscope (URF-V): Initial Experience, Urol. Annal.; (2011) vol. 3; pp. 133-137.

(Continued)

*Primary Examiner* — Timothy J Neal
(74) *Attorney, Agent, or Firm* — Myers Bigel, P.A.

(57) ABSTRACT

Methods for treating urinary (kidney) stones in patients using a small outer diameter ureteroscope may help overcome problems associated with conventional methods for removing kidney stones and may minimize patient discomfort, avoid hospitalization and reduce costs associated with more conventional surgical treatments of kidney stones. The methods can be carried out in an outpatient environment such as a urologists' office without requiring general anesthesia.

24 Claims, 3 Drawing Sheets

(51) Int. Cl.

| | |
|---|---|
| *A61B 18/26* | (2006.01) |
| *A61B 1/018* | (2006.01) |
| *A61B 1/307* | (2006.01) |
| *A61M 25/09* | (2006.01) |
| *A61B 17/22* | (2006.01) |
| *A61B 17/221* | (2006.01) |
| *A61B 1/01* | (2006.01) |
| *A61B 90/00* | (2016.01) |
| *A61B 18/00* | (2006.01) |

(52) U.S. Cl.
CPC ............. *A61B 2017/22084* (2013.01); *A61B 2018/00511* (2013.01); *A61B 2018/00982* (2013.01); *A61B 2090/3614* (2016.02); *A61B 2217/007* (2013.01)

(56) References Cited

U.S. PATENT DOCUMENTS

| | | | |
|---|---|---|---|
| 5,083,549 | A | 1/1992 | Cho et al. |
| 5,536,234 | A | 7/1996 | Newman |
| 6,458,076 | B1 | 10/2002 | Pruitt |
| 6,949,125 | B2 | 9/2005 | Robertson |
| 7,654,989 | B2* | 2/2010 | Knapp .................. A61B 1/307 604/284 |
| 2001/0041899 | A1 | 11/2001 | Foster |
| 2002/0115983 | A1 | 8/2002 | Sekino et al. |
| 2004/0199052 | A1 | 10/2004 | Banik et al. |
| 2006/0129030 | A1 | 6/2006 | Dehmel |
| 2006/0206004 | A1 | 9/2006 | Dehmel et al. |
| 2007/0038227 | A1 | 2/2007 | Massicotte et al. |
| 2008/0214895 | A1 | 9/2008 | Campos |
| 2009/0306546 | A1* | 12/2009 | Knapp ............... A61B 1/00147 600/585 |
| 2010/0137846 | A1 | 6/2010 | Desai et al. |
| 2010/0191053 | A1 | 7/2010 | Garcia et al. |
| 2010/0274344 | A1 | 10/2010 | Dusbabek et al. |
| 2012/0209062 | A1 | 8/2012 | Qiao |
| 2012/0209073 | A1* | 8/2012 | McWeeney ........ A61B 1/00071 600/146 |

FOREIGN PATENT DOCUMENTS

| | | |
|---|---|---|
| DE | 102010054422 | 6/2012 |
| EP | 2428157 | 3/2012 |

OTHER PUBLICATIONS

Bader et al., The Polyscope: A Modular Design, Semidisposable Flexible Ureteronoscope System; J. Endourology; (2011) vol. 24; pp. 1061-1066.
Bader et al., Contemporary Management of Ureteral Stones; Eur. Urology; (2012) vol. 61; pp. 764-772.
Bagley & Healy, History and Development of the Ureteroscope: What Does the Future Hold?, Urothiliasis (2012), pp. 333-341.
Cohen et al., Flexible Ureteroscopy: Wireless and Sheathless, Ureteroscopy: Indications, Instrumentation & Technique; (2013); pp. 291-302.
Flexible Fiberoptic Ureteroscope (URF-P6), Olympus, Product Summary, http://medical.olympusamerica.com/products/ureteroscope/fiberscope-urf-p5, printed from the internet Jul. 21, 2015, 2 pages.
Flexima™ Ureteral Catheters, Boston Scientific, Product Information, http://www.bostonscientific.com/en-US/products/catheters--ureteral/ . . . , printed from the internet Jun. 24, 2015, 4 pages.
International Search Report and Written Opinion from International Application No. PCT/US2014/025948, mailed Jul. 29, 2014.
Intravesical therapy for bladder cancer, American Cancer Society, General Information, http://www.cancer.org/cancer/bladdercancer/detailedguide/bladder-c . . . , date unknown but believed to be prior to the present application, printed from the internet Jun. 26, 2015, 2 pages.
Katz et al., Setting a New Standard for Topical Therapy of Upper-Tract Transitional-Cell Carcinoma: BCG and Interfereon-α2B*, Journal of Endourology, Apr. 2007, pp. 374-377, vol. 21, No. 4.
Nepple et al., Review of Topical Treatment of Upper Tract Urothelial Carcinoma, Advances in Urology, Hindawi Publishing Corporation, 2009, 6 pages, article ID 472831, http://dx.doi.org/1.1155/2009/472831.
Shapiro et al, Outcomes of Intrarenal Bacillus Calmette-Guérin/Interferon-α2B for Biopsy-Proven Upper-Tract Carcinoma in Situ, Journal of Endourology, Dec. 2012, pp. 1645-1650, vol. 26, No. 12.
U.S. Appl. No. 14/181,611, filed Feb. 14, 2014, Inventor(s): Nathaniel Michael Fried et al., 47 pages, which is a Continuation-In-Part of U.S. Appl. No. 13/752,893, filed Jan. 29, 2013.
U.S. Appl. No. 13/752,893, filed Jan. 29, 2013, Inventor Nathaniel Fried et al., 21 pages, which claims the benefit of U.S. Appl. No. 61/594,040, filed Feb. 2, 2012.

* cited by examiner

METHODS FOR THE MINIMALLY INVASIVE TREATMENT OF URINARY STONES

RELATED APPLICATION

This application is a divisional application of U.S. patent application Ser. No. 13/827,045 filed Mar. 14, 2013, the contents of which are hereby incorporated by reference as if recited in full herein.

FIELD

The present invention relates generally to devices and associated methods for the removal of urinary stones from a body cavity, and in particular, to devices and associated methods for removal of urinary stones as a truly outpatient procedure(non-hospital or office).

BACKGROUND

Kidney stones, which are also commonly known as urinary stones, are solid accumulations and aggregations of matter formed in the kidneys from minerals in the urine.

Urinary stones are typically classified by their location in the kidney, ureter, or bladder, or by their chemical composition. About 66% of those with kidney stones are men.

Kidney stones typically leave the body by passage in the urine stream, and many stones are formed and passed without causing symptoms. If stones grow to sufficient size (usually at least 3 millimeters (0.12 in)) they can cause obstruction of the ureter. Ureteral obstruction has many adverse side effects including discomfort, pain, and spasm of the ureter. In many cases, the pain is commonly felt in the flank (the area between the ribs and hip), lower abdomen, and groin (a condition called renal colic). In some instances, renal colic can be associated with nausea, vomiting, fever, blood in the urine, pus in the urine, and painful urination.

Currently, there are three primary treatment options that account for over 99% of the surgical treatments of kidney stones: 1) percutaneous nephrolithotomy (PNL), 2) shock wave lithotripsy (SWL), and 3) ureteroscopic stone removal (URS).

PNL is generally used for stones larger than about 20 mm in diameter, and is performed almost exclusively for large stones within the kidneys. SWL is generally used to treat moderate sized stones, for example, stones having diameters ranging from 5 to 20 mm. URS is commonly used for stones having diameters of less than 20 mm. While PNL is used exclusively in the kidneys, SWL and URS can be used to treat kidney stones in the kidney and the ureter.

In addition to the above techniques, medical expulsion therapy (MET) employs medications to assist in the natural passage of the stone. MET may improve the statistical likelihood of small stone (2-6 mm) passage provided the patient remains comfortable and stable.

However, this may require days to weeks of observation in an outpatient mode, waiting with uncertainty for a stone to pass. In the event the stone fails to pass, the patient will often require an operative treatment using URS or SWL. To date, no medications exist to dissolve stones, and stones 7 mm diameter or greater have less than 10% chance of passage.

SWL and URS are both typically outpatient procedures, as opposed to PNL, which requires a hospitalization of 1-2 days after surgery. SWL is typically performed with intravenous sedation (no formal anesthesia) with no instrumentation inserted into the patient. However, success rates, defined as stone-free with a single treatment session, generally do not exceed 75%. SWL typically depends on the availability of an expensive mobile machine that is rarely hospital owned, traveling around on a scheduled circuit, typically once weekly for most hospitals.

In contrast, URS is performed in the hospital operating room almost always with general anesthesia. URS is normally available on a daily 24/7 basis, with the insertion of a small fiberoptic telescope into the patient through the natural urinary channels (no incisions). The telescope is advanced up the ureter to the stone, where, if small enough (2-5 mm), it may be extracted intact. Otherwise the stone is fragmented in place with a laser fiber passed through the telescope. Fragments are then irrigated out or extracted mechanically with miniature instruments. Success or stone free rates for URS are 95-98% in experienced hands.

Due to the outpatient scheduling requirement for SWL, patient selection must be limited to those whose pain is well controlled and who have no other relatively common co-existent emergent contraindications that a stone may present, such as infection or kidney failure. These complicating factors demand a more urgent intervention than SWL can provide.

Unfortunately, there are currently no surgical treatments that are available as an outpatient in the urologist's office. Each of the above techniques requires formal sedation or anesthesia and the support of in-hospital environment (URS) or mobile lithotripsy unit (SWL). Both of these treatments also require the use of radiologic support in the form of fluoroscopy to monitor the treatment and technical progress during the procedure.

The relative status quo of the above surgical techniques for urologic stone disease has been the case now for approximately 15 years in the U.S. There have been no significant technological changes in PNL or SWL technology in over 20 years and no new advances are advertised or anticipated from known current research efforts. The most recent innovations in the triad of stone surgery occurred with URS, with the introduction of the first miniaturized flexible uretero-scope around 1995.

However, current ureteroscopes generally include a requisite mechanical structure so that they can be actively steered and directed through the ureter to the location of the stone, and into the kidney where active steerability of the ureteroscope is mandatory. As a consequence, the sizes of these ureteroscopes have been limited to minimum diameters ranging from 2.5 to 3.0 mm diameter (7.5-9 F). Currently, no passively flexible exists exclusively for ureteral stone surgery.

Current ureteroscopes rely on the use of laser lithotripsy to destroy stones by passing a tiny laser fiber through a channel within the telescope. The laser fiber transmits laser energy from a separate laser source located in proximity to the surgical field. The laser fiber then is placed in contact with a stone under direct vision and the surgeon reduces the stone to dust and tiny passable fragments. The ureteroscope is removed and the patient awakens, goes to a recovery nursing unit and is discharged home. The sizes of current ureteroscopes are such that the technique of introduction and manipulation would not be tolerated by an un-anesthetized patient.

Accordingly, there still exists a need for devices and associated methods that can be used to remove urinary stones as a truly outpatient procedure that can be performed in a non-hospital, office environment.

SUMMARY

Embodiments of the present invention are directed to passively flexible ureteroscopes having diameters of less than about 2.5 millimeters (mm), and in particular is about 2 mm or less. As a result, devices in accordance with embodiments of the present invention may help overcome many of the problems associated with the prior art devices and methods for removing kidney stones. In particular, the availability to surgically treat patients suffering from kidney stones as a non-hospital, truly outpatient procedure may help minimize patient pain and suffering as well as significantly reduce costs typically associated with the surgical treatment of kidney stones.

In one embodiment, the present invention is directed to a device for removing a stone from a body cavity comprising an elongate member having a distal portion, a proximal portion, and an inner conduit that extends longitudinally between the proximal and distal portions. The elongate member comprises a passively flexible material that is capable of being inserted and directed through a patient's body cavity, such as the ureter, by manual direction and pressure so that minimal, if any, additional mechanical or steering mechanisms are present. As a result, the diameter of the elongate member can be significantly reduced in comparison to convention ureteroscopes, which in turn, may permit the surgeon to surgically remover kidney stones from the ureter in a truly outpatient process. That is, without the need for hospitalization and anesthetization of the patient.

Suitable materials for the elongate member may include a wide variety of polymers including silicone rubber, nitinol, nylon, polyurethane, and polyethylene terephthalate (PETE) latex, polytetrafluoroethylene (TEFLON®), hydrophilic polymers, and thermoplastic elastomers. In one particular embodiment, the elongate member comprises a flexible silicone material. wherein the elongate member is passively flexible and has a diameter that is less than about 2.5 mm.

In one embodiment, the device also includes a port disposed towards the proximal portion of the elongate member and an opening disposed at the distal portion of the elongate member. The port and opening are in communication with each other via the conduit. The conduit, which functions as a working channel, can be used to introduce various devices, such as an irrigation tube, laser fiber, basket, and the like, into a desired location with respect to a targeted kidney stone. In one embodiment, the optical device comprises a charged coupled device or fiber optics.

In addition, the device includes an optical device disposed towards the proximal portion of the elongate member, and at least one light source disposed towards the proximal portion of the elongate member. The optical device and the light source cooperate to provide the surgeon images of the stone so that the laser fiber can be properly positioned and the surgeon can monitor the status of the procedure.

In some embodiments, the elongate member may include an outer coating comprising a hydrophilic material, such as polyurethane.

In a further aspect, the invention is directed to a method of removing a kidney stone from a patient in need thereof, the method comprising the steps of: inserting a cystoscope into a bladder of a patient; identifying a kidney stone in a ureter of the patient; positioning a guidewire in close proximity to the stone; providing a ureteroscope in accordance with at least one embodiment of the present invention; traveling the ureteroscope over the guidewire to position the ureteroscope in close proximity to the stone; removing the guidewire; obtaining an image of the ureter with the optical device of the ureteroscope; positioning the ureteroscope so that a center of mass of the stone is centered in the image; passing a laser fiber through the ureteroscope so that the laser fiber is in close proximity to the stone; activating the laser fiber to fragment the stone.

In some embodiments, the step of identifying the kidney stone may be performed with the assistance of an imaging procedure, such as fluoroscopic imaging.

Aspects of the present invention may provide advantages over currently available treatment methods for the treatment of kidneys stones. In particular, the availability to surgically treat patients suffering from kidney stones as a non-hospital, truly outpatient procedure may help minimize patient pain and suffering as well as significantly reduce costs typically associated with the surgical treatment of kidney stones.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
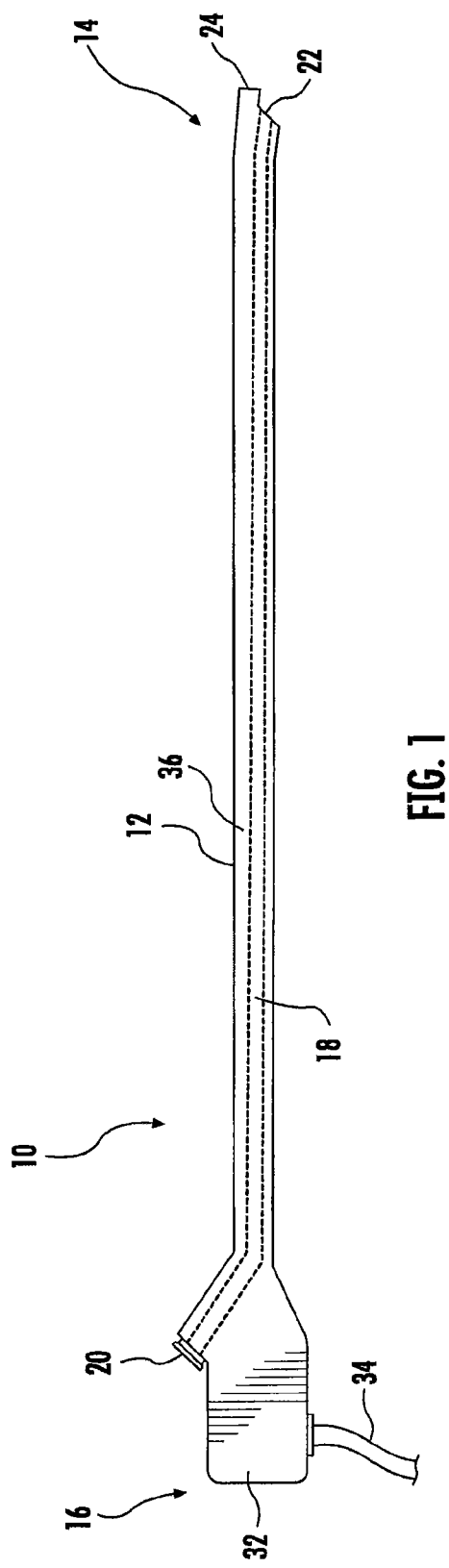
FIG. 1 is a side view of a device in accordance with at least one embodiment of the present invention.

With reference to FIG. 1, a device for removing a stone from a body cavity that is in accordance with at least one embodiment of the present invention is illustrated and designated with reference number 10. The device 10 comprises an elongate member 12 having a distal portion 14 and a proximal portion 16. The interior of the elongate member 12 includes a longitudinally extending conduit 18 (represented by the dashed lines in FIG. 1) that extends from a port 20 located towards the proximal portion 16 of the elongate member 12 and an opening 22 disposed at the distal portion 14 of the elongate member 12. The conduit is configured to provide communication between the port and the opening.

The elongate member comprises a passively flexible material so that the device can be inserted and directed through a patient's body cavity, such as the ureter, with minimal, if any, additional mechanical or steering mechanisms that are present in conventional ureteroscopes and cystoscopies. In other words, the term passively flexible means that the elongate material has sufficient flexibility so that it can be maneuvered through the ureter, or other body cavity, without the need for additional steering devices or associated mechanical structures. As a result, the diameter of the elongate member can be significantly reduced in comparison to conventional ureteroscopes. Suitable materials for the elongate member may include a wide variety of polymers including silicone rubber, nitinol, nylon, polyurethane, and polyethylene terephthalate (PETE) latex, polytetrafluoroethylene (TEFLON®), hydrophilic polymers, and thermoplastic elastomers. In one particular embodiment, the elongate member comprises a flexible silicone material. It should be recognized that in some embodiments, the elongate member may include some minimal steering devices and associated structures provided that the minimal size and flexibility of the device is maintained.

Figure 2A:
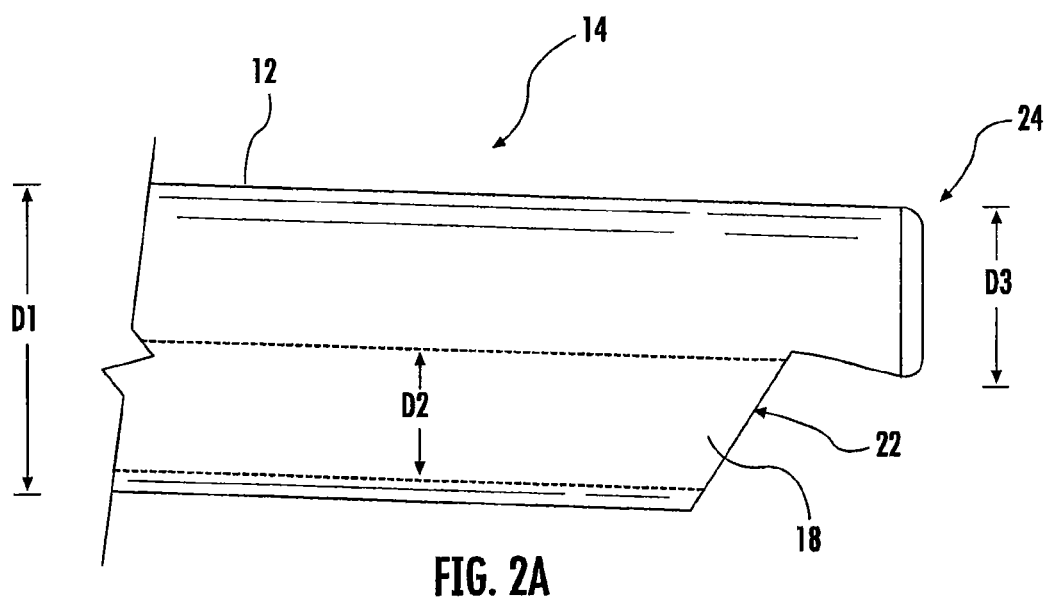
FIG. 2A is a partial side view of the distal portion of the device of FIG. 1.
Figure 2B:
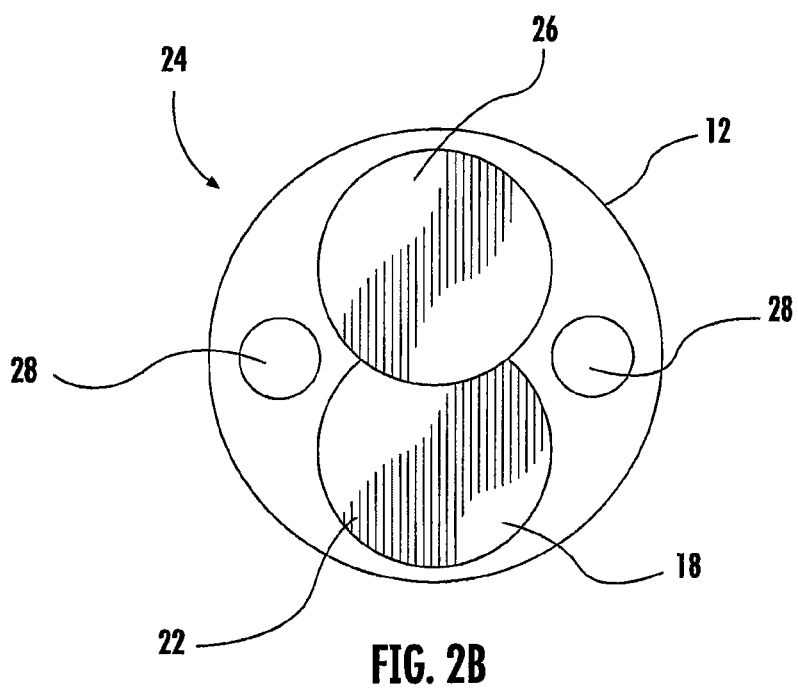
FIG. 2B is a front view of the distal portion of the device of FIG. 1.

Turning now to FIGS. 2A and 2B, a partial view of the elongate member is shown. As shown in FIG. 2A, the diameter D1 (or width) of the elongate member is generally less than about 2.5 millimeters (mm), and in particular is about 2 mm or less. In some embodiments, the diameter D1 is from about 1.7 to 2.2 mm, and more particularly, about 2 mm.

The diameter D2 (or width) of the conduit 18 is desirably large enough to allow for irrigation as well as the insertion of a guide wire or laser fiber. In some embodiments, the diameter D2 is less than 1.25 mm, and preferably less than about 1 mm, and more preferably, about 0.7 to 1 mm, with a size of about 1 mm being most preferred.

The overall length of the elongate member is desirably sufficient so that it can be inserted and directed to a desired location in a body cavity. For example, in applications directed to the removal of a kidney stone in the ureter, the length of the elongate member may range from about 35 to 55 centimeters (cm), and in particular, about 40 to 45 cm.

The distal portion of the elongate member defines a tip portion 24 of the device in which an optical device 26, such as a charged coupled device (CCD), camera, or optical fiber, and a light source 28 is positioned. In this regard, FIG. 2B shows a front view of the medical device 10 in which the light source 28 and optical device 26 are positioned in the tip portion 24 of the elongate member. The optical device and light source will typically be connected to an external power source, control device (e.g., a processor) via one or more connectors, such as wires, that extend through one or more additional conduits (not shown) that extend longitudinally through the elongate member.

In the illustrated embodiment, the light source and optical device are shown as being disposed above the opening 22 to the conduit. However, it should be recognized that other configurations may be utilized in the practice of the invention. As shown in FIG. 2A, the overall diameter D3 (or width) of the optical device may be about 1 to 1.5 mm, and in particular, about 1.1 to 1.3 mm. Preferably, the diameter D3 is about 1.2 mm or less.

The optical device 26 is generally positioned such that it is located for enabling imaging of forward regions of the body cavity in which the device is positioned. In one embodiment, optical device may be arranged for focusing incident light onto a CCD for generation of a signal which is communicated to an external display, for example a monitor, television or the like. The signal provided by the optical device is preferably digital, although other formats such as analogue signals may be used. In one embodiment, the signal is communicated to the display by conductors such as electrical wires or an optical fiber carrying a modulated signal.

Other embodiments may include wireless transmission means, for example a miniature radio transmitter, which is adapted to receive a signal from the optical device and transmit the signal through the body of the patient to a receiver located externally of the patient. This embodiment advantageously dispenses with the requirement for electrical conductors to connect the optical device to a display. In still other embodiments, the device may include a transmitter positioned towards a proximal portion of the device, such as in a handle, so that the signal can be transmitted from the transmitter to the display, such as through a radio transceiver or similar device. In this embodiment, the optical device may be connected to the transmitter through conductors, such as electrical wires.

In some embodiments, the optical device may comprise an optical fiber. In particular, visualization within the body cavity may be achieved utilizing one or more optic fibers arranged in the same manner as the electrical conductors associated with a CCD. Preferably, a bundle of optic fibers will be used. Generally, the optic fibers will terminate at the distal tip of the elongate member. In one embodiment, the distal ends of the optical fibers are arranged with one or more lenses held in the casing, for feeding light incident upon the lens into the fibers. The light is transmitted by means of internal reflection along the length of the optical fiber to proximal ends. Light processing means, such as processor, disposed at the proximal ends of the optical fibers receive the light and derive therefrom an image for display upon the display device in a manner known to those skilled in the art.

The light source is preferably disposed proximate the optical device, or is integral therewith, so as to illuminate the region of the body cavity to be imaged. In exemplary embodiments the light source takes the form of a miniature globe, a diode, or for instance an optical fiber positioned so as to communicate light from an external light source. In the case of optical fibers, the size of a bundle of optical fibers may generally have a diameter from about 0.25 to 0.6 mm and, in particular, from about 0.4 to 0.5 mm.

Referring back to FIG. 1, the device 10 may include a handle 32 disposed towards the proximal end of the elongate member. The handle may also include an inlet/outlet 34 for one or more conductors, such as wires, for providing power and communications to the light source and optical device. In an alternative embodiment, the handle may include a power source, such as a battery, and a transceiver for facilitating wireless communication between the optical device and an external display device.

In one embodiment, the outer surface 36 of the elongate member may include an outer sheath, such as a polymeric coating, that substantially covers the outer surface of the elongate member. In one embodiment, the sheath may comprise a polymer coating including but not limited to such substances as polyurethane (e.g., polyurethane 55D and 90A) or polytetrafluoroethylene, or silicone. In a preferred embodiment, the sheath includes a hydrophilic coating.

As noted previously, the conduit 18 is desirably large enough to allow for irrigation as well as the insertion of a guide wire or laser fiber. In particular, the conduit also commonly referred to as a "working channel" provides a means through which the body cavity can be irrigated via a saline or similar solution, and means for positioning a laser fiber in close proximity to a stone to be targeted for removal. The port 20 through which access to the conduit is obtained, can be any conventional port, such as a standard Luer-lok. In one embodiment, an irrigation tubing can be introduced into the conduit via the port.

Figure 3:
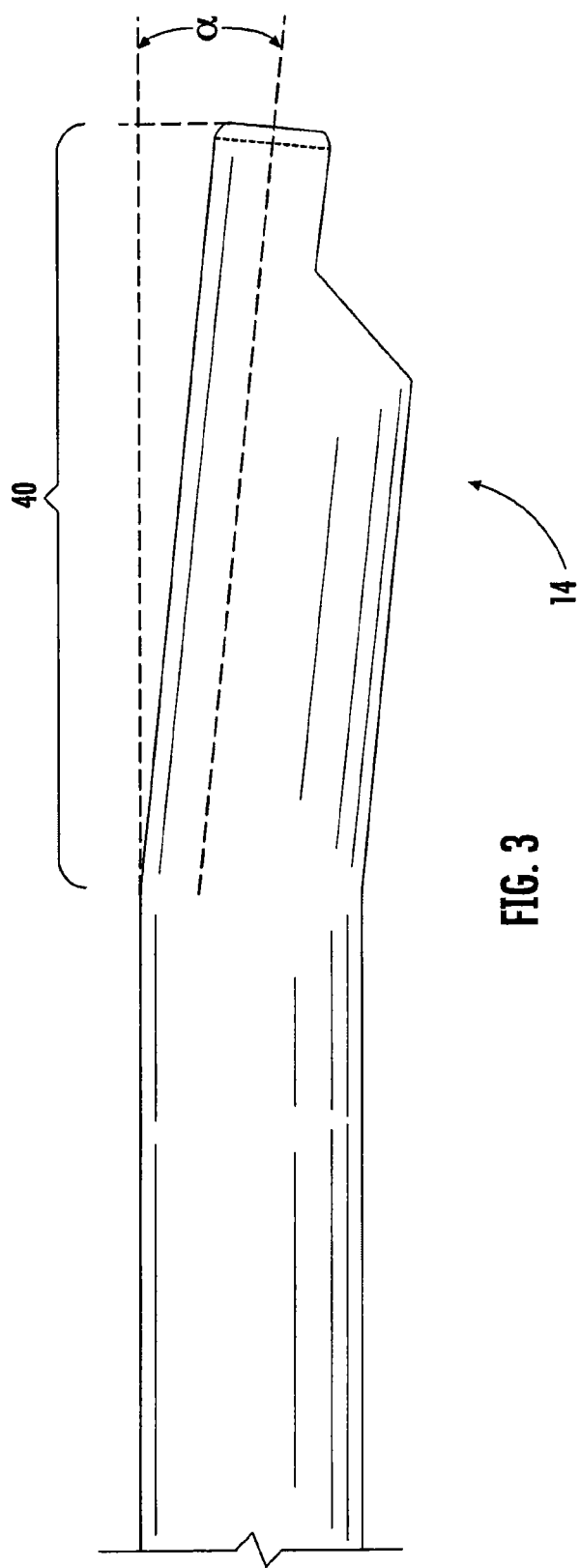
FIG. 3 is a partial side view on alternative embodiment of the device of FIG. 1.

In some embodiments, the distal portion of the elongate member may be slightly angled so as to provide better maneuvering and positioning of the medical device within the body cavity. In this regard, FIG. 3 illustrates an embodiment of the invention in which the distal portion of the elongate member includes an angled portion 40 that is slightly angled relative to the remaining portion of the elongate member. As shown in FIG. 3 the angle defined by the angled portion is identified as angle α. Angle α can generally range from about 3° to 8°, and in particular is about 5°. With rotational manipulation of the slightly angled tip, the tip may be directed in a 360° fashion to address a stone in the lumen of the ureter.

Advantageously, medical devices in accordance with the present invention can be used to treat patients suffering from kidney stones of less than 20 mm. As a result, the invention may help avoid problems associated with prior treatment methods that typically require hospitalization.

In a typical procedure according to the present invention, the patient undergoes conscious sedation (with or without supplemental oral sedation) while in the supine position (male patient) or lithotomy position (female patient). Initial endoscopy on the patient is then performed with a standard flexible cystoscope, also using local gel anesthesia as per standard current outpatient or office protocol. The cystoscope is advanced per urethra into the bladder and the bladder is inspected. The location of the stone within the ureter is identified and confirmed. Preferably, the location is confirmed by pre-procedural imaging.

In some embodiments, it may also be desirable to perform this part of the procedure with the assistance of fluoroscopic imaging. Radiographic (fluoroscopic) study of the involved ureter may be performed by the gentle retrograde injection of contrast into the ureteral orifice in the bladder through a standard ureteral catheter, such as a 5F catheter (retrograde ureterogram).

After the stone has been located and identified, a guidewire is advanced through the working channel of the cystoscope. In one particular embodiment, the guidewire (e.g., a standard GLIDEWIRE®) may be advanced through the previously inserted catheter. Preferably the guidewire is a standard 0.035" or less (e.g., from 0.025"-0.035") hydrophilic guidewire. Once the guidewire is positioned in the desired location relative to the stone, the catheter is removed leaving the guidewire in place. In an alternative embodiment, the cystoscope may also be removed at this time.

The device 10 (also referred to herein as a ureteroscope) is now passed over the guidewire and into the bladder and up the ureter until the stone is encountered. In a preferred embodiment, positioning of the ureteroscope is assisted with fluoroscopic imaging. The guidewire is now removed and irrigation (normal saline) is initiated through the conduit of the ureteroscope.

The ureteroscope may be now be manipulated either forward or backward by the surgeon's hand. Rotational manipulation may be achieved by the use of a modified torque device (e.g., Cook Urological) applied to the ureteroscope. The optical device of the ureteroscope can now be used to obtain images of the patient's ureter with the assistance of the light source. As noted previously, the optical device is configured to provide images via a display device.

By a combination of longitudinal and rotational manipulation, the stone will be engaged in a "center of mass" view. Once a satisfactory "sight picture" is achieved with the optical device wherein the stone is centered in view, a laser fiber (e.g., standard 270 micron holmium laser fiber) will be passed through the conduit of the ureteroscope. With the laser fiber in direct contact with the stone, the laser is activated and fired at standard energy settings (typically 6-10 Hz at 600-800 mJ). Once the stone is fragmented sufficiently, the laser will be discontinued and removed from the ureteroscope. Stone fragments may be cleared by passage of a 1.9F stone basket through the conduit and withdrawing the fragments into the bladder. At this point, the ureteroscope can be removed from within the patient.

In a further aspect of the invention, a ureteral stent (6F) can be positioned in the patient's ureter. In this aspect, (the cystoscope is reintroduced if previously removed) and a guidewire is then passed into the ureter under fluoroscopic imaging. The guidewire is then advanced to the level of the kidney. A ureteral stent (6F) is then passed over the guidewire until a proximal end of the stent is in the kidney, and a distal end of the stent remains in the bladder. At this point the cystoscope is removed and the procedure is completed.

Generally, it may be desirable to monitor the patient in a holding area for up to one hour and discharged home to follow-up in one week. The stent ensures that the ureter remains patent in the post-procedure period until the patient returns to the office for follow-up. This is typically after one week for a brief removal of the stent in similar fashion using the cystoscope, requiring only local topical gel anesthesia.

From the foregoing discussion, it is evident that the present invention provides many advantages over currently available treatment methods for the treatment of kidneys stones. In particular, the availability to surgically treat patients suffering from kidney stones as a non-hospital, truly outpatient procedure may help minimize patient pain and suffering as well as significantly reduce costs typically associated with the surgical treatment of kidney stones.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of removing a kidney stone from a patient in need thereof, the method comprising:
   inserting a cystoscope into a bladder of a patient;
   identifying a kidney stone in a ureter of the patient;
   positioning a guidewire in close proximity to the stone;
   providing a ureteroscope with an elongate member having a distal portion and an opposing proximal portion with a longitudinally extending conduit extending through an interior of the elongate member, wherein the elongate member has a maximal outer diameter that is 2.0 mm to about 1.7 mm over a length extending between the proximal portion and the distal portion;
   traveling the conduit of the ureteroscope over the guidewire to position the distal portion of the elongate member of the ureteroscope in close proximity to the stone;
   removing the guidewire;
   obtaining an image of the ureter with an optical device of the ureteroscope;
   positioning the ureteroscope so that a center of mass of the stone is centered in the image;
   passing a laser fiber through the conduit of the ureteroscope so that the laser fiber is in close proximity to or directly contacts the stone; and
   activating a laser in communication with the laser fiber to fragment the stone.

2. The method of claim 1, wherein the method is carried out without the need for general anesthesia.

3. The method of claim 1, wherein the traveling and/or positioning of the ureteroscope comprises longitudinally and rotationally manipulating the ureteroscope, wherein the method further comprises removing the laser fiber from the conduit of the ureteroscope after the stone is fragmented, then passing a stone basket through the conduit and withdrawing the fragments into a bladder of the patient, then removing the ureteroscope from the patient.

4. The method of claim 1, further comprising removing the cystoscope from the patient once the guidewire is in position before traveling the ureteroscope to the stone.

5. The method of claim 1, wherein the conduit defines a single working channel of the ureteroscope and extends to an external port proximate the proximal portion of the elongate member, and wherein the method is carried out to dispense liquid for irrigation of a treatment site associated with the stone while the laser fiber is in the conduit the dispensed liquid introduced via the port of the conduit.

6. The method of claim 1, wherein the distal portion of the elongate member has a distalmost tip and the conduit channel terminates a distance behind the tip, wherein the tip holds the optical device and at least one light source, and wherein the image is obtained while illuminating the stone using the at least one light source.

7. The method of claim 6, wherein the at least one light source includes first and second light sources arranged with the optical device therebetween.

8. The method of claim 7, wherein the first and second light sources comprise optical fibers, wherein the conduit is a single working channel of the ureteroscope and has a diameter of between about 0.7 mm and 1 mm, and wherein the optical device has a diameter between 1 mm to 1.5 mm.

9. The method of claim 1, wherein the maximal outer diameter of the elongate member extends for a length of between 35-55 centimeters between the proximal and distal portions.

10. A method of removing a kidney stone from a patient in need thereof, the method comprising:
providing a ureteroscope with a single working channel in an elongate member having a distal portion and an opposing proximal portion with a longitudinally extending working channel extending through an interior of the elongate member between an external port and an open distal end, wherein the elongate member has a maximal outer diameter that is 2.0 mm to about 1.7 mm over a length extending between the proximal portion and the distal portion, and wherein the maximal outer diameter of the elongate member extends for a length of between 35-55 centimeters between the proximal and distal portions;
inserting a cystoscope into a bladder of a patient;
identifying a kidney stone in a ureter of the patient;
positioning a guidewire in close proximity to the stone;
guiding the ureteroscope using the guidewire to position the distal portion of the elongate member of the ureteroscope in close proximity to a target treatment site comprising the stone;
obtaining an image of the ureter with an optical device held by the ureteroscope;
passing a laser fiber through the working channel of the ureteroscope to the target treatment site so that the laser fiber is in close proximity to or directly contacts the stone;
activating a laser in communication with the laser fiber to fragment the stone while the laser fiber is in close proximity to or directly contacts the stone; and
irrigating the target treatment site by introducing irrigation liquid into the port and through the working channel.

11. The method of claim 10, wherein the inserting, identifying, positioning, guiding, obtaining, passing, activating and irrigating steps are carried out without general anesthesia.

12. The method of claim 10, wherein the guiding of the ureteroscope comprises longitudinally and rotationally manipulating the ureteroscope.

13. The method of claim 10, wherein the method further comprises:
removing the guidewire from the working channel before passing the laser fiber through the working channel;
removing the laser fiber from the working channel of the ureteroscope after the stone is fragmented;
then passing a stone basket through the working channel and withdrawing the fragments into the bladder of the patient; and
then removing the ureteroscope from the patient after the irrigation.

14. The method of claim 13, further comprising, after withdrawing the fragments, placing a ureteral stent into the ureter with proximal and distal ends positioned in a kidney and the bladder, respectively.

15. The method of claim 10, further comprising removing the cystoscope from the patient once the guidewire is in position before guiding the ureteroscope to the stone.

16. The method of claim 10, wherein the distal portion of the elongate member has a distalmost tip and the working channel terminates a distance behind the tip, wherein the tip holds the optical device and at least one light source, and wherein the image is obtained while illuminating the stone using the at least one light source.

17. The method of claim 16, wherein the at least one light source includes first and second light sources arranged with the optical device therebetween.

18. The method of claim 10, further comprising illuminating the target treatment site with at least one light source held by the distal end portion of the ureteroscope while obtaining the image.

19. The method of claim 18, wherein the working channel has a diameter of between about 0.7 mm and 1 mm, and wherein the optical device has a diameter between 1 mm to 1.5 mm.

20. A method of removing a kidney stone from a patient in need thereof, the method comprising:
positioning a guidewire in close proximity to a kidney stone in a ureter of the patient;
providing a ureteroscope with an elongate member having a distal portion and an opposing proximal portion with a longitudinally extending conduit extending through an interior of the elongate member, wherein the elongate member has a maximal outer diameter that is 2.0 mm to 1.7 mm over a length of 35-55 centimeters extending between the proximal portion and the distal portion;
traveling the ureteroscope into the patient using the guidewire to position the distal portion of the elongate member of the ureteroscope in close proximity to the stone;
obtaining at least one image of the ureter with an optical device of the ureteroscope;

passing a laser fiber through the conduit of the ureteroscope so that the laser fiber is in close proximity to the stone; and fragmenting the stone by activating a laser in communication with the laser fiber.

21. The method of claim 20, wherein the method is carried without the need for general anesthesia.

22. The method of claim 21, wherein the method is carried out in an outpatient non-hospital environment.

23. The method of claim 20, further comprising, after the fragmenting, withdrawing the fragments, then placing a ureteral stent into the ureter with proximal and distal ends positioned in a kidney and a bladder, respectively.

24. The method of claim 20 wherein the conduit defines a single working channel of the ureteroscope and extends to an external port proximate the proximal portion of the elongate member, and wherein the method is carried out to remove the guidewire before the laser fiber is passed through the conduit, then dispense liquid introduced via the port of the conduit to irrigate a treatment site associated with the stone while the laser fiber is in the conduit.

* * * * *

UNITED STATES PATENT AND TRADEMARK OFFICE
CERTIFICATE OF CORRECTION

PATENT NO. : 9,655,678 B2
APPLICATION NO. : 15/215067
DATED : May 23, 2017
INVENTOR(S) : Irby, III Page 1 of 1

It is certified that error appears in the above-identified patent and that said Letters Patent is hereby corrected as shown below:

In the Claims

Column 9, Claim 5, Line 20:
Please correct "in the conduit the"
To read:
-- in the conduit, the --

Signed and Sealed this
Fifth Day of June, 2018

Andrei Iancu
*Director of the United States Patent and Trademark Office*